US00PP32556P2

(12) United States Plant Patent
Ault

(10) Patent No.: US PP32,556 P2
(45) Date of Patent: Dec. 1, 2020

(54) ***ASTER* PLANT NAMED 'BILLOWING PINK'**

(50) Latin Name: ***Aster* hybrid**
Varietal Denomination: Billowing Pink

(71) Applicant: James Robert Ault, Libertyville, IL (US)

(72) Inventor: James Robert Ault, Libertyville, IL (US)

(73) Assignee: CHICAGOLAND GROWS, INC, Glencoe, IL (US)

( * ) Notice: Subject to any disclaimer, the term of this patent is extended or adjusted under 35 U.S.C. 154(b) by 0 days.

(21) Appl. No.: 16/873,166

(22) Filed: Feb. 19, 2020

(51) Int. Cl.
*A01H 6/14* (2018.01)
*A01H 5/02* (2018.01)

(52) U.S. Cl.
USPC ..... Plt./355

(58) Field of Classification Search
USPC ..... Plt./355
CPC ..... A01H 5/02; A01H 6/14
See application file for complete search history.

*Primary Examiner* — Annette H Para
(74) *Attorney, Agent, or Firm* — Penny J. Aguirre

(57) ABSTRACT

A new cultivar of *Aster* plant named 'Billowing Pink' that is characterized by its uniform, rounded and dense mounded plant habit, its clumping forming growth habit, its sticky, aromatic foliage that is not appealing to deer or rabbits, its very good resistance to rust, powdery mildew and lace bug predation, and its inflorescences with ray florets that are wider in size and pink-violet in color with the color persistent for the duration of bloom and strongly upturned at inception and remain somewhat upturned throughout the blooming period.

2 Drawing Sheets

Botanical classification: *Aster* hybrid.
Variety denomination: 'Billowing Pink'.

CROSS REFERENCE TO A RELATED APPLICATION

This application is co-pending with a U.S. Plant Patent Application filed for a plant derived from the same breeding program that is entitled *Aster* Plant Named 'Billowing Violet' (U.S. Plant patent application Ser. No. 16/873,171).

BACKGROUND OF THE INVENTION

The present invention relates to a new and distinct cultivar of *Aster* of hybrid origin, botanically known as *Aster* 'Billowing Pink', and will be referred to hereafter by its cultivar name, 'Billowing Pink'. 'Billowing Pink' is a new herbaceous perennial suitable for landscape plantings.

The new cultivar is the result of a controlled breeding program conducted by the Inventor in Glencoe, Ill. The intent of the program is to develop new cultivars of *Aster* that are hardy in U.S.D.A. Zone 5, disease resistant, unpalatable to deer and rabbits, provide a diversity of desirable flower traits and plant habits. The new cultivar arose from crosses made with an unnamed and unpatented seedling of *Aster oblongifolius* in September of 2012 as the female parent and pooled pollen from unnamed and unpatented plants *Aster* plants of hybrid origin from the Inventor's breeding program as the male parent. The exact male parent is therefore unknown. 'Billowing Pink' was selected as a single unique plant from the resulting seedlings of the cross in October of 2015.

The new cultivar was first asexually propagated by shoot tip cuttings by the Inventor in Glencoe, Ill. in June of 2016. Asexual propagation by shoot tip cuttings and division has determined that the characteristics of this cultivar are stable and are reproduced true to type in successive generations.

SUMMARY OF THE INVENTION

The following traits have been repeatedly observed and represent the characteristics of the new *Aster*. These attributes in combination distinguish 'Billowing Pink' as a unique cultivar of *Aster*.

1. 'Billowing Pink' exhibits a uniform, rounded and dense mounded plant habit.
2. 'Billowing Pink' exhibits a clumping forming growth habit.
3. 'Billowing Pink' exhibits sticky, aromatic foliage that is not appealing to deer or rabbits.
4. 'Billowing Pink' exhibits very good resistance to rust, powdery mildew and lace bug predation when grown in comparison trials with other cultivars of *Aster*.
5. 'Billowing Pink' exhibits inflorescences with ray florets that are wide in size and pink-violet in color with the color persistent for the duration of bloom.
6. 'Billowing Pink' exhibits ray florets that are strongly upturned at inception and remain somewhat upturned throughout the blooming period.

The seed parent of 'Billowing Pink', differs from 'Billowing Pink' in having a larger height and spread, an earlier and longer blooming period, and ray florets that are slightly upturned at inception becoming horizontal to slightly downturned as they age. The possible pollen parents of 'Billowing Pink' all differ from 'Billowing Pink' in having larger capitula and either more open upright plant habits or lower, more dense and more rounded plant habits. 'Billowing Pink' can be most closely compared to *Aster oblongifolius* varieties 'Raydon's Birthday Pink' (not patented) and 'Dream of Beauty' (not patented). Both cultivars are similar to 'Billowing Pink' in having ray florets that are pink-violet in color and in producing sticky, aromatic foliage that deters rabbits and deer. 'Raydon's Birthday Pink' differs from 'Billowing Pink' in having an earlier blooming period, a larger plant size, ray florets that are narrower, and a more irregular and open plant habit. 'Dream of Beauty' differs from 'Billowing Pink' in having an earlier blooming period, a smaller plant size, a more irregular and open plant habit, and in being susceptible to lace bug damage.

BRIEF DESCRIPTION OF THE DRAWINGS

The accompanying colored photographs were taken in October and illustrate the overall appearance and distinct characteristics of the new *Aster* as grown outdoors in a trial plot in Glencoe, Ill.

The photograph in FIG. 1 was taken of a plant 5 years in age and provides a view of the plant habit of 'Billowing Pink' in bloom.

Figure 1:
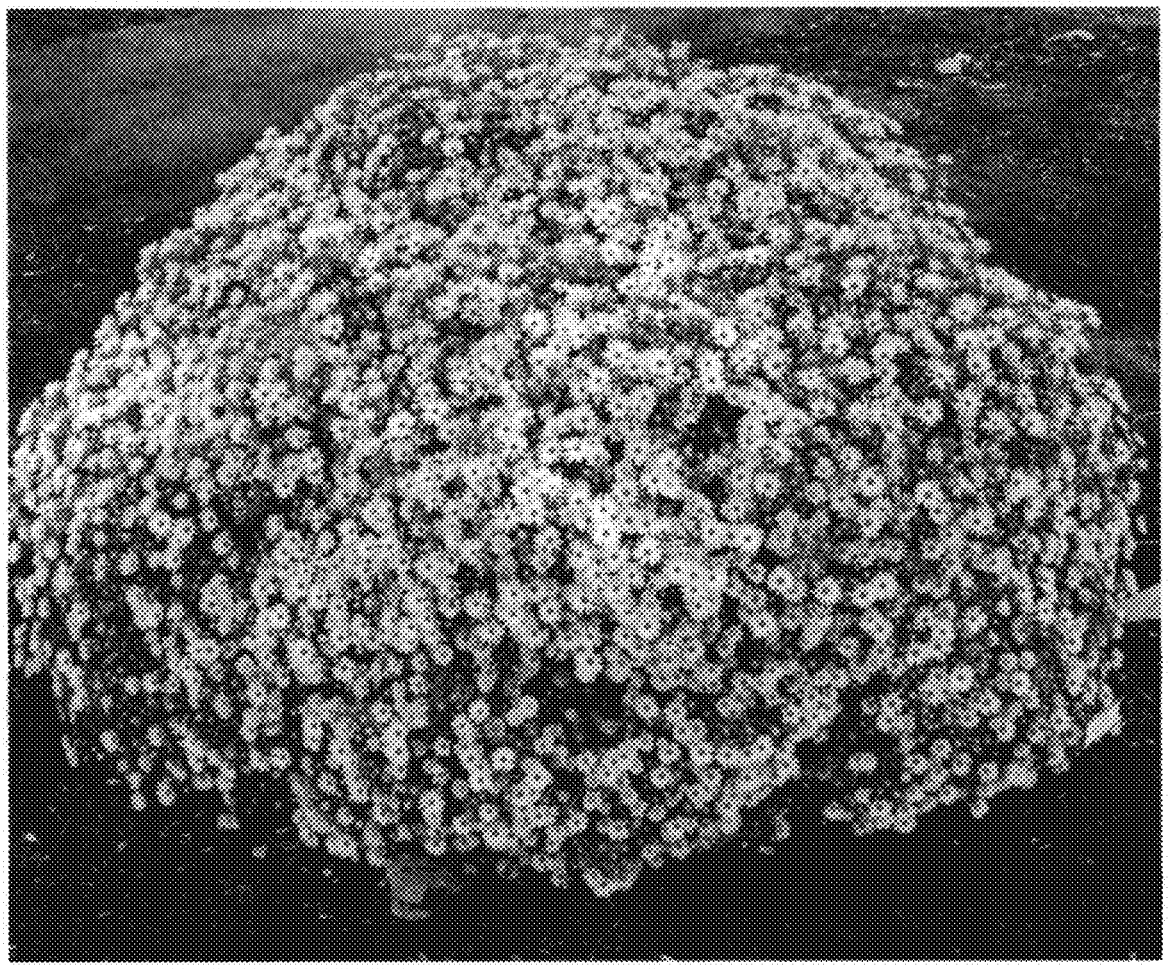
Figure 2:
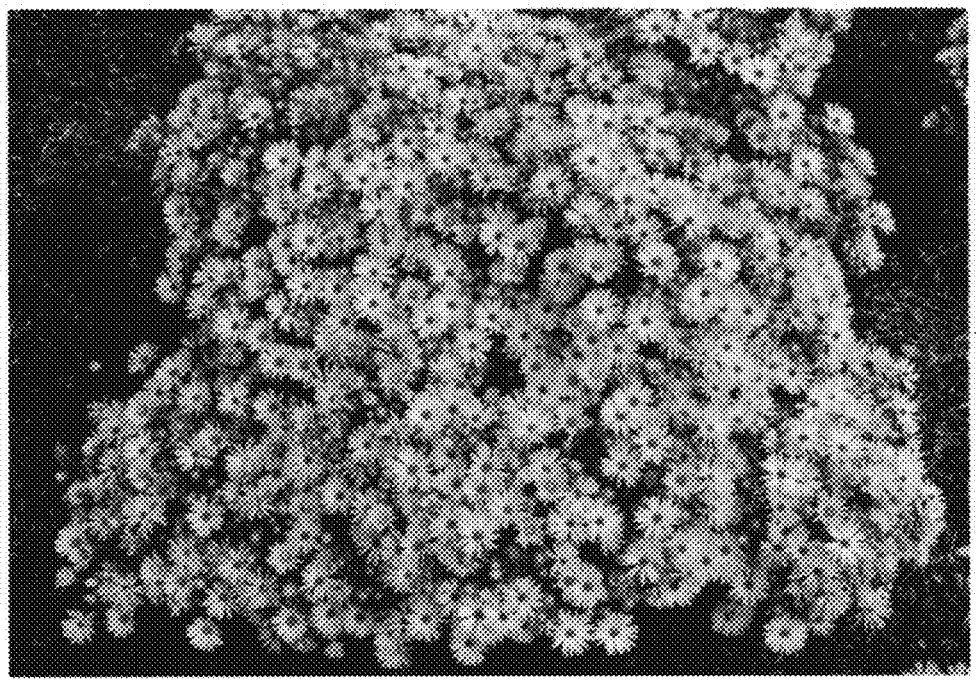

The photograph in FIG. 2 was taken of a plant 2 years in age and provides a top view of 'Billowing Pink' in bloom.

Figure 3:
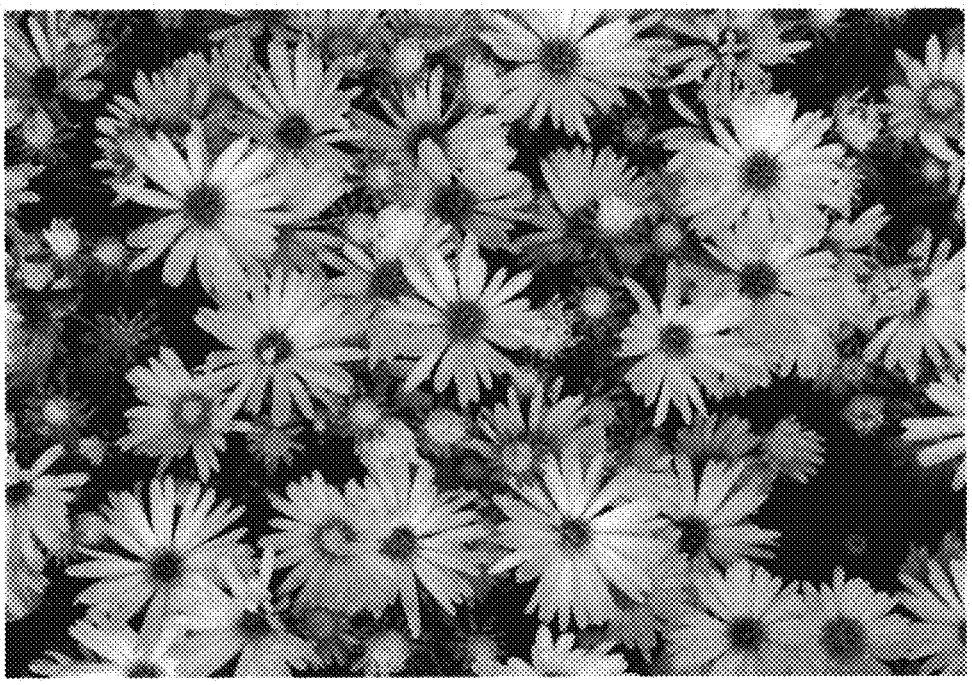

The photograph in FIG. 3 was taken of a plant 2 years in age and provides a close up view of the flowers of 'Billowing Pink'.

The colors in the photographs are as close as possible with digital photography techniques available, the color values cited in the detailed botanical description accurately describe the colors of the new *Aster*.

DETAILED BOTANICAL DESCRIPTION

The following is a description of one-year old plants of the new cultivar as grown outdoors in 2-quart containers in Glencoe, Ill. The description of the plant habit and mature height and spread were observed on 4-year-old plants of the new cultivar as grown in a trial bed in Glencoe, Ill. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming season*.—Typically for 6 weeks commencing in late September to early October and completing in mid-November in northern Illinois.

*Plant type*.—Herbaceous perennial.

*Plant habit*.—Uniform dense mound.

*Height and spread*.—2-year-old plants grown in the ground; average of 27 cm in length, 45 cm in width, 4-year-old plants grown in the ground; average of 66 cm in height and 122 cm in width.

*Hardiness*.—At least in U.S.D.A. Zones 4 to 7.

*Diseases and pest resistance*.—Has shown very good resistance to powdery mildew (*Golovinomyces asterum* var. *asterum*), rust (*Coleosporium asterum* and *Puccina* sp. and lace bug (*Corythuca marmorata*) predation.

*Root description*.—Fibrous.

*Propagation*.—Shoot tip cuttings and division.

*Root development*.—About 6 weeks to produce a rooted cutting, a rooted cutting planted in June will produce blooming plants 28 cm in height and 42 cm in width in the same growing season.

*Growth rate*.—Vigorous.

Stem description:

*Stem color*.—New growth; 145A, mature growth; a blend of N199B and N199C.

*Stem surface*.—Young stems; matte and glabrous, mature stems; glabrous and glossy.

*Stem size*.—Main stem; about 30 cm in length and 6 mm in width, lateral branches; average of 17 cm in length and 1 mm in width.

*Branching habit*.—1 main stem with an average of 26 horizontal lateral branches, whorled arrangement.

*Branch internode length*.—Average of 1 cm between lateral branches.

Foliage description:

*Leaf division*.—Simple.

*Leaf shape*.—Linear.

*Leaf base*.—Truncate.

*Leaf apex*.—Acute.

*Leaf margin*.—Entire.

*Internode length*.—Average of 3 mm.

*Leaf venation*.—Linear, not conspicuous, midrib recessed on upper surface, coloration same as leaf.

*Leaf attachment*.—Sessile.

*Leaf arrangement*.—Alternate.

*Leaf number*.—Average of 20 per stem 15 cm in length.

*Leaf surface*.—Both surfaces glabrous, matte and slightly rough to the touch.

*Leaf color*.—Young and mature, upper and lower surface; 144A.

*Leaf size* (*fully expanded*).—Up to 3 cm in length and 1 cm in width.

*Leaf fragrance*.—None.

Flower description:

*Inflorescence type*.—Composite, 1 to 3 capitula per flowering branchlet.

*Lastingness of individual capitula*.—Temperature dependent, under normal field conditions during the fall, typically last about 2 weeks.

*Fragrance*.—Slight and pleasant.

*Quantity of capitula*.—About 400 per plant in a 2-quart container.

*Capitula buds*.—About 6 mm in depth and 5 mm in diameter, oblong in shape, blend of 13A and 10D in color.

*Capitula size*.—About 3.2 cm in diameter and 5 mm in depth, disk is about 6 mm in diameter.

*Peduncle*.—Held at about a 45° angle to flowering branchlet, texture is glossy and glabrous, an average of 2.5 cm in length and 0.8 mm in width, color is 144A, an average of 12 leaves with similar in characteristics to lateral branch leaves.

*Involucral bracts* (*phyllaries*).—About 16, 137A in color, linear in shape, about 7 mm in length and 1 mm in width, inner and outer surface slightly glossy.

Ray florets (pistillate):

*Number*.—Average of 35.

*Shape*.—Oblanceolatc.

*Aspect*.—Primarily outward to nearly horizontal.

*Size*.—Average of 1.3 cm in length and 2.5 mm in width.

*Petal apex*.—Rounded.

*Petal base*.—Attenuate.

*Petal margins*.—Entire.

*Petal texture*.—Smooth, glabrous on upper and lower surface.

*Petal color*.—When opening upper and lower surface; base and mid-section 3C and 4D, tips 75C and 75D, when fully open upper surface; 84B, base 84A, when opening lower surface; 84C with slight undertones of 85C.

Disk florets (perfect):

*Quantity*.—Average of 40.

*Shape*.—Tubular.

*Size*.—About 3 mm in length and 0.05 mm in width.

*Color*.—16A.

Reproductive organs:

*Presence*.—Disk flowers are perfect, ray flowers are carpellate.

*Gynoecium*.—1 Pistil per disk and ray floret, style is 6 mm in length and 16C in color.

*Androecium*.—5 stamens per disk floret, fused into tube, anther is 16A in color with filament 11C in color, pollen was not observed.

*Fruit and seed*.—None observed.

It is claimed:

1. A new and distinct cultivar of *Aster* plant named 'Billowing Pink' as described and illustrated herein.

* * * * *